United States Patent [19]
Schoendorfer

[11] Patent Number: 6,033,561
[45] Date of Patent: Mar. 7, 2000

[54] APHERESIS SYSTEM INCORPORATING ALTERNATIVE SITE FOR ANTICOAGULANT ADDITION

[75] Inventor: Donald W. Schoendorfer, Santa Ana, Calif.

[73] Assignee: Baxter International Inc., Deerfield, Ill.

[21] Appl. No.: 08/410,940

[22] Filed: Mar. 27, 1995

Related U.S. Application Data

[63] Continuation of application No. 08/019,002, Feb. 18, 1993, abandoned.

[51] Int. Cl.[7] .............................. A61M 1/34; A61M 1/38; B01D 36/00
[52] U.S. Cl. ...................... 210/195.1; 210/85; 210/258; 210/416.1; 210/433.1; 210/500.24; 604/4; 604/5; 604/6
[58] Field of Search .................. 210/90, 97, 143, 210/195.2, 216, 217, 257.2, 297, 321.67, 321.68, 359, 258, 360.1, 433.1, 195.1, 416.1, 500.24, 645, 646, 650, 651, 929, 85; 604/4, 5, 6

[56] References Cited

U.S. PATENT DOCUMENTS

| | | | |
|---|---|---|---|
| 4,362,155 | 12/1982 | Skurkovich .................................. | 604/4 |
| 4,447,191 | 5/1984 | Bilstad et al. ................................ | 604/6 |
| 4,581,010 | 4/1986 | Skurkovich et al. ........................ | 604/4 |
| 4,605,394 | 8/1986 | Skurkovich ................................. | 604/4 |
| 4,708,714 | 11/1987 | Larsson et al. ............................. | 604/5 |
| 4,755,300 | 7/1988 | Fischel et al. ............................ | 210/650 |
| 4,776,964 | 10/1988 | Schoendorfer et al. .................. | 210/782 |
| 4,806,247 | 2/1989 | Schoendorfer et al. ............. | 210/360.1 |
| 4,808,307 | 2/1989 | Fischel et al. ...................... | 210/321.68 |
| 4,824,432 | 4/1989 | Skurkovich et al. ........................ | 604/4 |
| 4,851,126 | 7/1989 | Schoendorfer ........................... | 210/651 |
| 4,865,841 | 9/1989 | Balint, Jr. et al. ...................... | 424/85.8 |
| 4,871,462 | 10/1989 | Fischel et al. ............................ | 210/651 |
| 4,923,439 | 5/1990 | Seidel et al. ................................ | 604/6 |
| 5,034,135 | 7/1991 | Fischel ..................................... | 210/651 |
| 5,135,667 | 8/1992 | Schoendorfer ........................... | 210/782 |
| 5,171,456 | 12/1992 | Hwang et al. ........................... | 210/782 |
| 5,178,603 | 1/1993 | Prince ......................................... | 604/4 |
| 5,194,145 | 3/1993 | Schoendorfer ...................... | 210/321.68 |
| 5,211,849 | 5/1993 | Kitaevich et al. .......................... | 604/6 |
| 5,244,654 | 9/1993 | Narayanan ......................... | 210/500.24 |
| 5,254,248 | 10/1993 | Nakamura .......................... | 210/321.68 |
| 5,254,249 | 10/1993 | Terada et al. ..................... | 210/500.24 |

FOREIGN PATENT DOCUMENTS

| | | |
|---|---|---|
| 0106026 | 4/1984 | European Pat. Off. . |
| 0423369 | 4/1991 | European Pat. Off. . |
| 0496547 | 7/1995 | European Pat. Off. . |
| WO 86/05999 | 10/1986 | WIPO . |

*Primary Examiner*—John Kim
*Attorney, Agent, or Firm*—Robert D. Buyan; Denise M. Serewicz; Bradford R. L. Price

[57] ABSTRACT

An extracorporeal blood processing method and system wherein blood is extracted from a mammalian subject through a blood withdrawal tube having a blood pump, such as a peristaltic pump, positioned thereon. A "distal segment" of the blood withdrawal tube extends from the mammalian subject to the inlet side or withdrawal pump. A "proximal segment" of the blood withdrawal tube extends from the outlet side of the blood pump to an extracorporeal blood processing apparatus. An anticoagulant feed tube is connected to the "proximal segment" of the blood withdrawal tube such that a flow of anticoagulant solution may be combined with blood exiting the outlet of said blood pump and passing through the "proximal segment" of said blood withdrawal tubing.

6 Claims, 6 Drawing Sheets

APHERESIS SYSTEM INCORPORATING ALTERNATIVE SITE FOR ANTICOAGULANT ADDITION

This is a continuation of application(s) Ser. No. 08/019,002 filed on Feb. 18, 1993, now abandoned.

FIELD OF THE INVENTION

The present invention pertains generally to medical devices, and more particularly to a method and device for separating fluid, such as whole blood, into two or more separate constituent portions or fractions.

BACKGROUND OF THE INVENTION

The prior art has included numerous methods and devices for separating fluids, such as whole blood, into two or more specific components or constituent fractions.

The term "apheresis" describes a three-step procedure wherein whole blood is: (a) withdrawn; (b) separated into two or more fractions; and (c) at least one of the separated blood fractions is retransfused into the patient or donor. The most common type of apheresis procedure is known as "plasmapheresis". In plasmapheresis a quantity of liquid plasma is separated from a "cell concentrate" comprising the remaining liquid and cellular constituents of the blood and such cell concentrate is, thereafter, retransfused into the donor. Other types of apheresis procedures include "leukapheresis" (wherein leukocytes are separated from the whole blood) and "thrombocytapheresis" (wherein platelets are separated from the whole blood). Some apheresis procedures are carried out to effect harvesting and isolation of commercially usable blood components. Other apheresis procedures are carried out for therapeutic purposes. Examples of therapeutic procedures include "therapeutic plasma exchange" (wherein the blood plasma is removed and replaced by a substitute fluid) and various experimental procedures wherein a specific fraction of the blood is isolated and subjected to extracorporeal treatment, such as radiotherapy, chemotherapy, chelation therapy, or adsorptive removal of specific substances by passing the isolated blood fraction through an adsorptive column or the like.

Modern apheresis procedures are typically performed through the use of automated, electronically-controlled, apheresis instruments. Examples of commercially available automated apheresis instruments include the Autopheresis-C® system (Baxter Healthcare Corporation, Fenwal Division, 1425 Lake Cook Road, Deerfield, Ill. 60015), and the (Haemonetics Corporation, City, State).

In general, the automated apheresis instruments of the prior art utilize one or more extracorporeal blood separation apparatus such as a rotation, membrane or centrifugal separator. Such blood separation apparatus is fluidly connected to a blood vessel of the donor/patient by way of a blood extraction tube. A blood pump, such as a peristaltic pump, is positioned on the blood extraction tube to pump of the whole blood from the donor/patient to the blood separation apparatus. Typically, the blood extraction pump is positioned midway between the point at which blood is withdrawn from the donor/patient (e.g., the venipuncture site) and the point at which the blood enters the extracorporeal separation apparatus (e.g., the inlet). A "distal segment" of the blood extraction tube carries the withdrawn blood from the donor/patient to the blood pump. A "proximal segment" of the blood extraction tube carries the blood from the blood pump to the separation apparatus. In the prior art apheresis instruments, it is common procedure to add a flow of anticoagulant solution (e.g. heparin-saline or warfrin-saline) into the "distal segment" of the blood extraction tube at a location close to the vascular access point. Such addition of anticoagulant solution near the vascular access point serves to prevent clotting or coagulation of the blood as it subsequently passes through the extracorporeal apheresis system. This addition of anticoagulant solution is typically accomplished by providing a bag or container of anticoagulant solution connected to the "distal segment" of the blood extraction tube by way of an anticoagulant solution delivery tube. An anticoagulant pump, such as a peristaltic pump, may be positioned on the anticoagulant delivery tube to pump a metered amount of anticoagulant solution through said anticoagulant delivery tube and into the distal end of the "distal segment" of the blood extraction tube to accomplish the desired anticoagulation effect.

One drawback associated with the practice of adding the anticoagulant solution to the extracted blood at a site within the "distal segment" of the blood extraction tube is that any air bubbles or air inclusions within the anticoagulant feed tube are likely to be drawn directly into the "distal segment" of the blood extraction tube by the drawing action of the blood pump. Such air bubbles or air inclusion will then be carried through the blood pump and into the "proximal segment" of the blood extraction tube. Such air bubbles or air inclusions may then travel through the extracorporeal system until they reach a point at which they are detected, by direct observation, or by way of an electronic air detector located within the extracorporeal system. Such drawing of air bubbles into the system through the anticoagulant delivery tube has been known to occur as a result of inadvertent depletion of the anticoagulant solution within the anticoagulant bag or container. Such drawing of air bubbles through the anticoagulant feed tube may also occur due to inadvertent puncture or disconnection of the anticoagulant feed tube itself.

In view of the adverse effects associated with the above-described inadvertent entrainment of air within the extracorporeal apheresis system, there exists a need in the art for improved methodology and apparatus whereby anticoagulant solution may be effectively added to blood within an extracorporeal apheresis system with minimal or no likelihood of inadvertent entrainment of air bubbles into the extracorporeal system.

SUMMARY OF THE INVENTION

The present invention provides an apheresis method and system wherein blood is extracted from a donor/patient, through a blood extraction tube having a blood pump, such as a peristaltic pump, positioned thereon. The withdrawn blood is carried through the blood extraction tube to an extracorporeal blood separator apparatus and/or other attendant portions of an extracorporeal apheresis circuit. Two separate segments of the blood extraction tube are definable—a "distal segment" extending from the donor/patient to the blood pump and a "proximal segment" extending from the blood pump to the separation apparatus. In accordance with the invention, an anticoagulant feed tube is fluidly connected to the "proximal segment" of the blood extraction tube (i.e. between the blood pump and the separation apparatus). An anticoagulant pump or other pressure exerting apparatus is utilized to maintain a pressurized flow of anticoagulant through the anticoagulant feed tube. The pressure of anticoagulant within the anticoagulant feed tube is preferably slightly greater than the pressure of blood within the "proximal segment" of the blood extraction tube. As such, any inadvertent depletion of the anticoagulant supply or passage of a significant quantity of air into the anticoagulant feed tube will result in a backup of blood into the anticoagulant feed tube, rather than aspiration or pulling of the air from the anticoagulant feed tube into the blood extraction tube.

Further, in accordance with the invention, an anticoagulant agent such as heparin may be applied as a coating on the luminal surfaces of the "distal segment" of tubing or otherwise contained or impregnated in the blood contacting position of the distal segment of tubing so as to inhibit clotting of the blood from the time it is withdrawn from the blood vessel until it becomes mixed with anticoagulant solution from the anticoagulant feed tube.

Further, in accordance with the invention there is provided an automated extracorporeal apheresis system incorporating an anticoagulant feed component of the foregoing character and construction.

Further objects and advantages of the invention will become apparent to those skilled in the art upon reading and understanding of the following detailed description and the accompanying drawings.

DETAILED DESCRIPTION OF THE PREFERRED EMBODIMENTS

The following detailed description and the accompanying drawings are provided for purposes of describing and showing presently preferred embodiments of the invention only, and are not intended to describe or illustrate the only embodiments by which the present invention may be practiced or utilized. Accordingly, the following detailed description and the accompanying drawings are not intended to constitute, and shall not constitute, any limitation on the scope of the disclosure or claims of this patent application.

The present invention is an extracorporeal apheresis method and device wherein whole blood is withdrawn from a mammalian donor or patient, through a blood extraction tube to an extracorporeal blood separation apparatus. A blood extraction pump, such as a peristaltic pump, is positioned on the blood extraction tube to pump the blood from the vascular access site to the extracorporeal separation apparatus. Anticoagulant solution is added to the blood extraction tube at a location on the output side of the blood pump, rather than on the inlet side of the blood pump. Such anticoagulant addition to the blood extraction tube on the output side of the blood pump serves to prevent any air bubbles within the anticoagulant feed tube from being drawn into the blood extraction tube or other components of the extracorporeal apheresis system.

i. A Single Needle-Intermittent Flow System of the Invention

Figure 1:
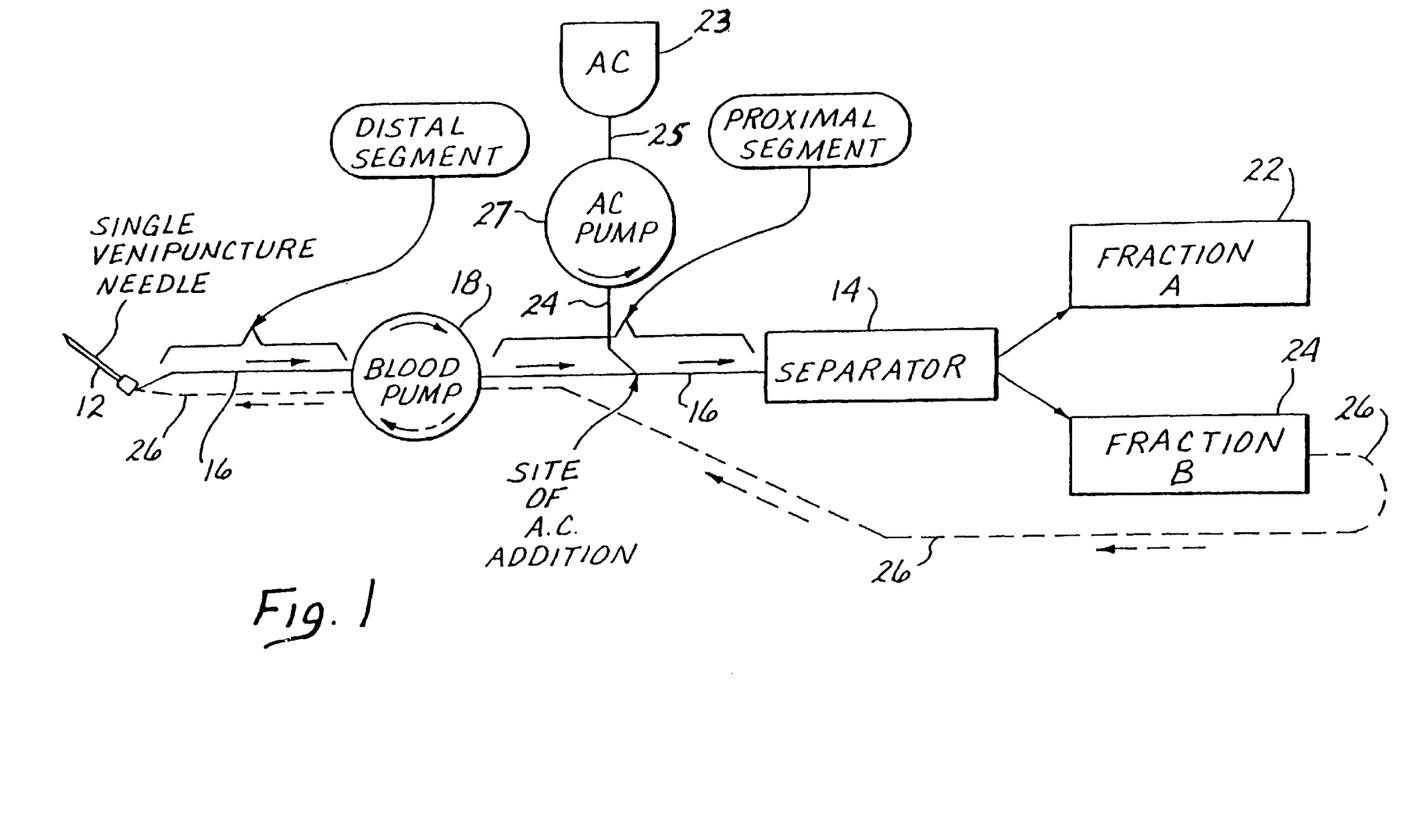
FIG. 1 is a schematic diagram of an intermittent flow, single-needle apheresis system of the present invention wherein a) blood extraction and b) blood/fluid reinfusion are accomplished alternately through a single venipuncture needle or vascular access point.

FIG. 1 is a schematic diagram of an intermittent flow, single-needle apheresis method and device of the present invention comprising a single venipuncture needle 12 fluidly connected to an extracorporeal blood separator apparatus 14 by way of a blood extraction tube 16. The extracorporeal blood separation apparatus 14 may comprise various types of separation apparatus including centrifugal separators, semi-permeable membranes, rotating membrane separators and the like. Examples of commercially available blood separation apparatus 14 useable in the device of the present invention include the plasma cell-C™ separator and the platelet cell separator (Baxter Healthcare Corporation, Fenwal Division, 1425 Lake Cook Road, Deerfield, Ill. 60015). Examples of blood separator apparatus useable in the device of the present invention are further described in U.S. Pat. Nos. 4,851,126 (Schoendorfer) entitled APPARATUS AND METHODS FOR GENERATING PLATELET CONCENTRATE; 5,034,135 (Fischel) entitled BLOOD FRACTIONATION SYSTEM AND METHOD; 4,871,462 (Fischel, et al.) entitled ENHANCED SEPARATION OF BLOOD COMPONENTS; 4,755,300 (Fischel, et al.) entitled COUETTE MEMBRANE FILTRATION APPARATUS FOR SEPARATING SUSPENDED COMPONENTS IN A FLUID MEDIUM USING HIGH SHEAR; 4,808,307 (Fischel, et al.) entitled COUETTE MEMBRANE FILTRATION APPARATUS FOR SEPARATING SUSPENDED COMPONENTS IN A FLUID MEDIUMS USING HIGH SHEAR; and 4,776,964 (Schoendorfer, et al.) entitled CLOSED HEMAPHERESIS SYSTEM AND METHOD, the entire disclosures of said United States Patents being expressly incorporated herein by reference.

The blood extraction tube 16 carries blood from the venipuncture needle 12 to the blood separator apparatus 14. A blood pump 18 is positioned on the blood extraction tube 16 to pump the blood from the venipuncture needle 12 to the separator apparatus 14. The blood pump 18 may comprise any type of blood pump capable of propelling the blood through the blood extraction tube 16 from the venipuncture needle 12 to the separator apparatus 14. It is preferable that the blood pump 18 be capable of effecting the desired pumping of the blood through blood extraction tube 16 without unnecessary or undue damage to the cellular constituents of the blood. Additionally, it is preferable that the blood pump 18 be capable of pumping the blood through blood extraction tube 16 without imparting microbial or other contaminants to the blood. Accordingly, in many embodiments of the invention, the blood pump 18 will comprise a peristaltic pump operative to create peristaltic movements in the walls of the blood extraction tube 16, thereby creating the desired pumping effect of blood through blood extraction tube 16.

The blood pump 18 is positioned on the blood extraction tube 16 at a location between the single venipuncture needle 12 and the blood separator apparatus 14. Thus, the blood extraction tube 16 includes a first or distal segment extending from the single venipuncture needle 12 to the inlet side of the blood pump 18 and a second or proximal segment extending from the outlet of the blood pump 18 to the separator apparatus 14. The pressure and flow dynamics within the first or distal segment of the blood extraction tube 16 will differ from the pressure or flow dynamics within the second or proximal segment of the blood extraction tube 16 in that blood carried through the first or distal segment is being pulled or drawn into the blood pump 18 while blood within the second or proximal segment is being propelled, under positive pressure, from the outlet of blood pump 18.

An anticoagulant source or container 23 is connected to the second or proximal segment of blood extraction tube 16 by way of an anticoagulant feed tube 25. As such, anticoagulant solution is carried from the anticoagulant container 23 through anticoagulant feed tube 25 and enters the second or proximal segment of the anticoagulant feed tube 16 at a site between the outlet of the blood pump 18 and the inlet of the separator apparatus 14. In some embodiments, the anticoagulant 23 may be added by gravity drip or by pressurization of a flexible anticoagulant container 23. In other embodiments, such as the system shown in FIG. 1, an anticoagulant metering pump 26 is positioned on the anticoagulant feed tube 25 to effect continuous pumping of a metered amount of anticoagulant through feed tube 25 and into the second or proximal segment of the blood extraction tube 16. The anticoagulant metering pump 27 may be electronically connected to and coordinated with blood pump 18 so as to pump anticoagulant solution through anticoagulant feed tube 25 only at such times as blood is being pumped from the patient/donor to the blood separator apparatus 14 by way of blood extraction tube 16.

In the embodiment shown in FIG. 1, the blood separator apparatus 14 is utilized to separate the blood into a first fraction or "Fraction A" and a second fraction or "Fraction B". In the embodiment shown, Fraction A is separated to a Fraction A container 22 and subsequently discarded or subjected to separate processing for harvesting of desired blood products. Fraction B is pooled or retained in a Fraction B container 24 and intermittently reinfused into the patient/donor via reinfusion tube 26. In the embodiment shown in FIG. 1, the reinfusion tube 26 is mounted on or passed through blood pump 18 and blood pump 18 is alternately operable in a reinfusion mode whereby blood pump 18 may be utilized to intermittently pump the contents of Fraction B container 24 through reinfusion tube 26 and back into the patient/donor through the single venipuncture needle 12.

In a typical plasmapheresis system the "Fraction A" shown in FIG. 1 would comprise liquid blood plasma while the "Fraction B" would comprise cell concentrate. The liquid plasma of Fraction A would be collected in a collection vessel and subsequently removed for secondary processing (e.g., fresh freezing or lyophilization) or processing (e.g., isolation of blood products such as Factor VIII). The cell concentrate of "Fraction B" would be intermittently returned to the donor by way of reinfusion tube 26.

ii. A Dual-Needle Continuous Flow System of the Invention

Figure 2:
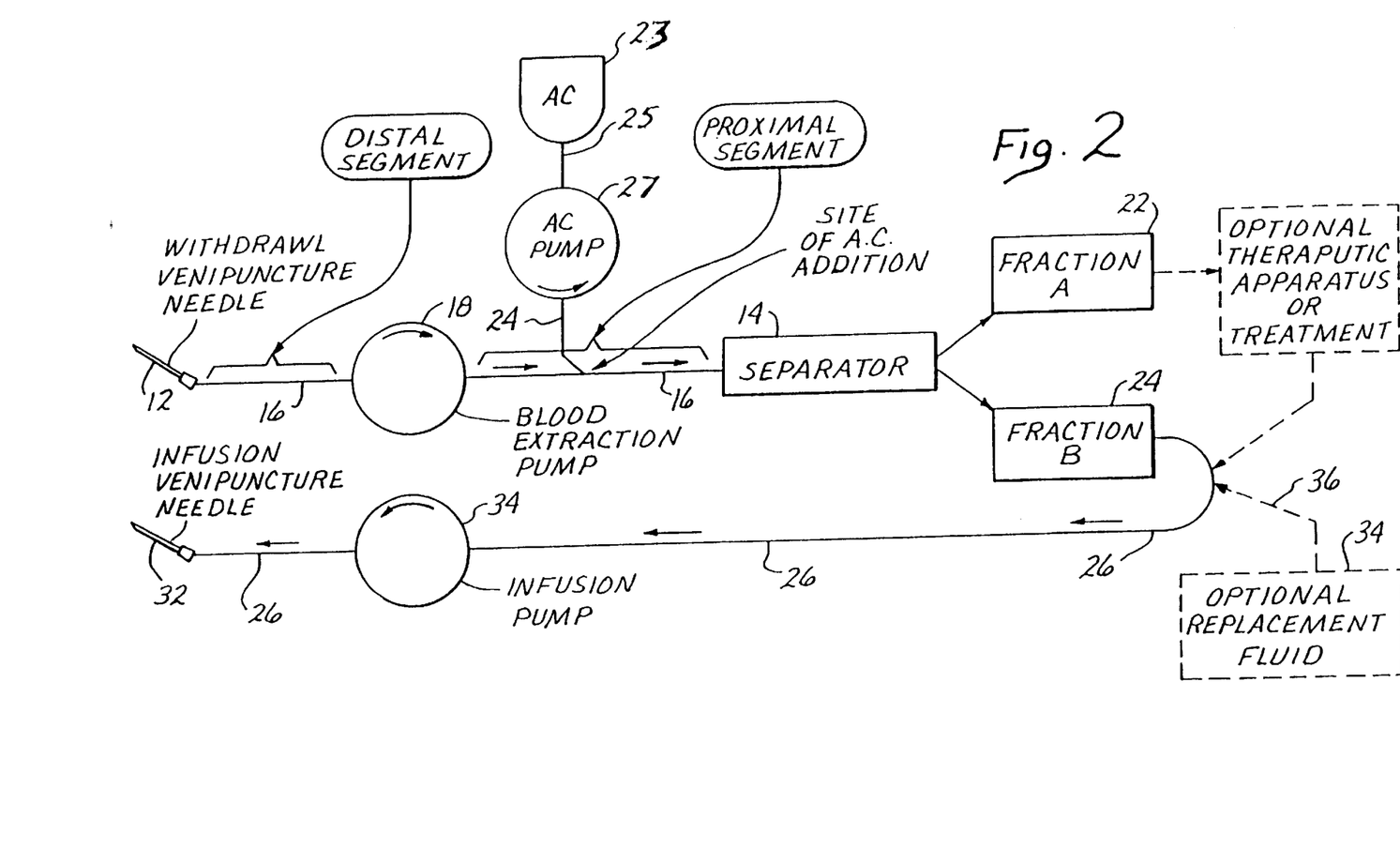
FIG. 2 is a schematic diagram of a continuous flow, dual-needle apheresis system of the present invention whereby blood is withdrawn through a first venipuncture needle and blood or other fluid is infused through a second venipuncture needle.

FIG. 2 is a schematic diagram of a continuous flow, dual-needle apheresis method and device of the present invention. Similar to the single needle embodiment shown in FIG. 1, the dual-needle embodiment shown in FIG. 2 employs a withdrawal venipuncture needle 12 fluidly connected to an extracorporeal blood separators 14 by way of a blood extraction tube 16. Blood pump 18 is mounted on the blood extraction tube 16 to effect pumping of blood from the withdrawal venipuncture needle 12 to the extracorporeal blood separator apparatus 14 in the manner described hereabove with respect to the single needle intermittent flow embodiment shown in FIG. 1.

Also, as in the single-needle, intermittent flow embodiment shown in FIG. 1, an anticoagulant source or container 23 is connected to the second or proximal segment of the blood extraction tube 16 by way of an anticoagulant feed tube 25. An optional anticoagulant metering pump 26 may be utilized to provide a metered flow of anticoagulant solution from anticoagulant solution source or container 22 into the second or proximal segment of the blood extraction tube 16. As in the above-described single-needle intermittent flow embodiment, the pressure of blood passing through the second or proximal segment of the blood extraction tube 16 is sufficiently high relative to any air or gas inclusions passing through anticoagulant feed tube 24 to prevent such air or gas inclusions from entering the blood extraction tube 16. Rather, the pressurized blood within the second or proximal segment of the blood extraction tube 16 will compress any air or gas inclusions within anticoagulant feed tube 24, thereby causing blood from the second or proximal segment of the blood extraction tube 16 to undergo retrograde flow into the anticoagulant feed tube 24 and thereby preventing inadvertent entrainment or entry of air or gas from anticoagulant feed tube 24 into blood extraction tube 16. The dual-needle continuous flow system shown in FIG. 2 differs from the single-needle intermittent flow system of FIG. 1 in that the "Fraction B" component of the blood is carried through reinfusion tube 26 to a separate reinfusion venipuncture needle 32. The separate reinfusion venipuncture needle 32 provides a second vascular access point separate and apart from the location of the withdrawal venipuncture needle 12. As such, the "Fraction B" component may be continuously reinfused into the patient through separate infusion venipuncture needle 32. To facilitate such reinfusion of the "Fraction B" component into the patient/donor an infusion pump 34 may be positioned on reinfusion tube 26 to effect pumping of the "Fraction B" component through reinfusion tube 26 and into the patient/donor through infusion venipuncture needle 32. The infusion pump 34 may comprise any suitable type of pump and, in particular, may comprise a peristaltic pump of the type described hereabove for use as the blood extraction pump 18.

In some applications of the dual-needle continuous flow system shown in FIG. 2, the "Fraction A" component of the blood will be discarded or removed for subsequent processing. In such applications wherein the "Fraction A" component is removed, it may be desirable to add a replacement fluid, such as donor plasma or saline solution, to the "Fraction B" component prior to reinfusion thereof. Toward this end, an optional replacement fluid source or container 34 may be connected to reinfusion tube 26 by way of a replacement fluid tube 36. Suitable gravity feed, pressurization or pumping apparatus may be utilized to provide the desired flow rate of replacement fluid from optional replacement fluid source or container 35 through line 36 and into reinfusion tube 26.

Because of its continuous flow capability, the system shown in FIG. 2 is particularly suitable for therapeutic applications wherein it is desired to a) separate a specific fraction or constituent of the blood (e.g., cell free plasma or leukocyte rich plasma), b) subject such separated blood fraction or constituent to a therapeutic treatment modality (e.g., column adsorption, chemotherapy, radiotherapy, phototherapy, etc. . . . ), and c) subsequently recombine the therapeutically treated blood fraction or component with the remaining fractions or components of the whole blood, for subsequent reinfusion back into the patient.

Figure 3:
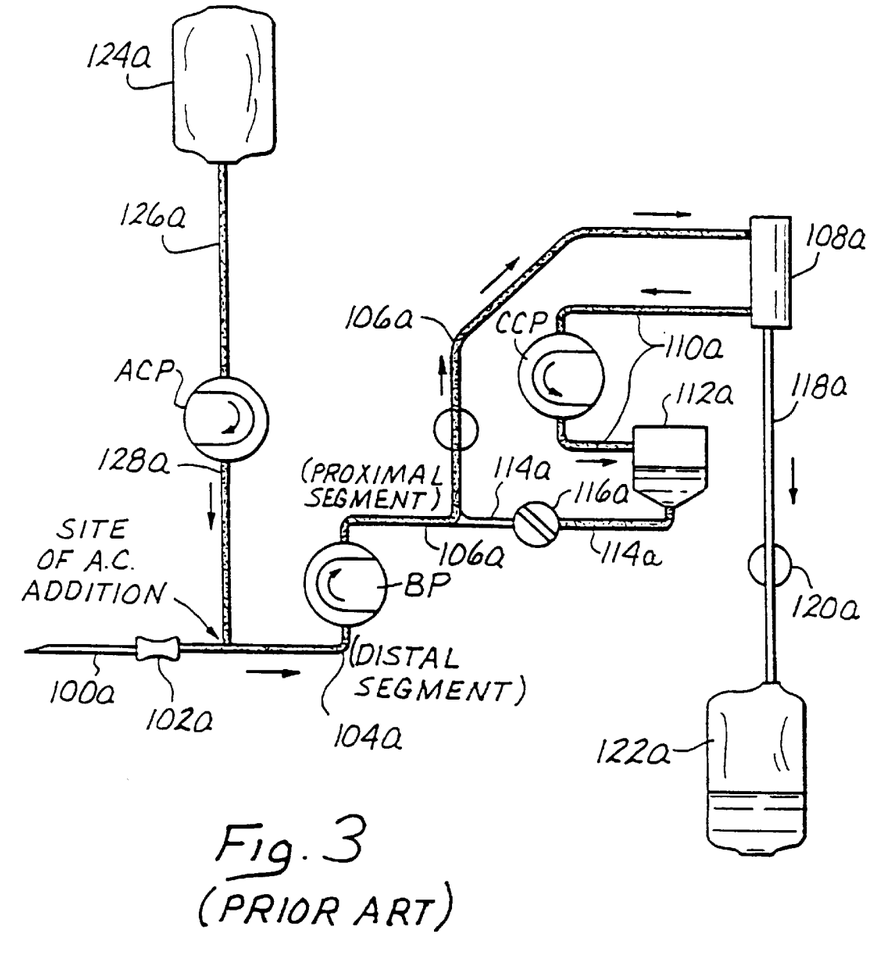
FIG. 3 is a component diagram of an automated, single-needle apheresis instrument of the prior art being operated in a blood withdrawal mode.
Figure 4:
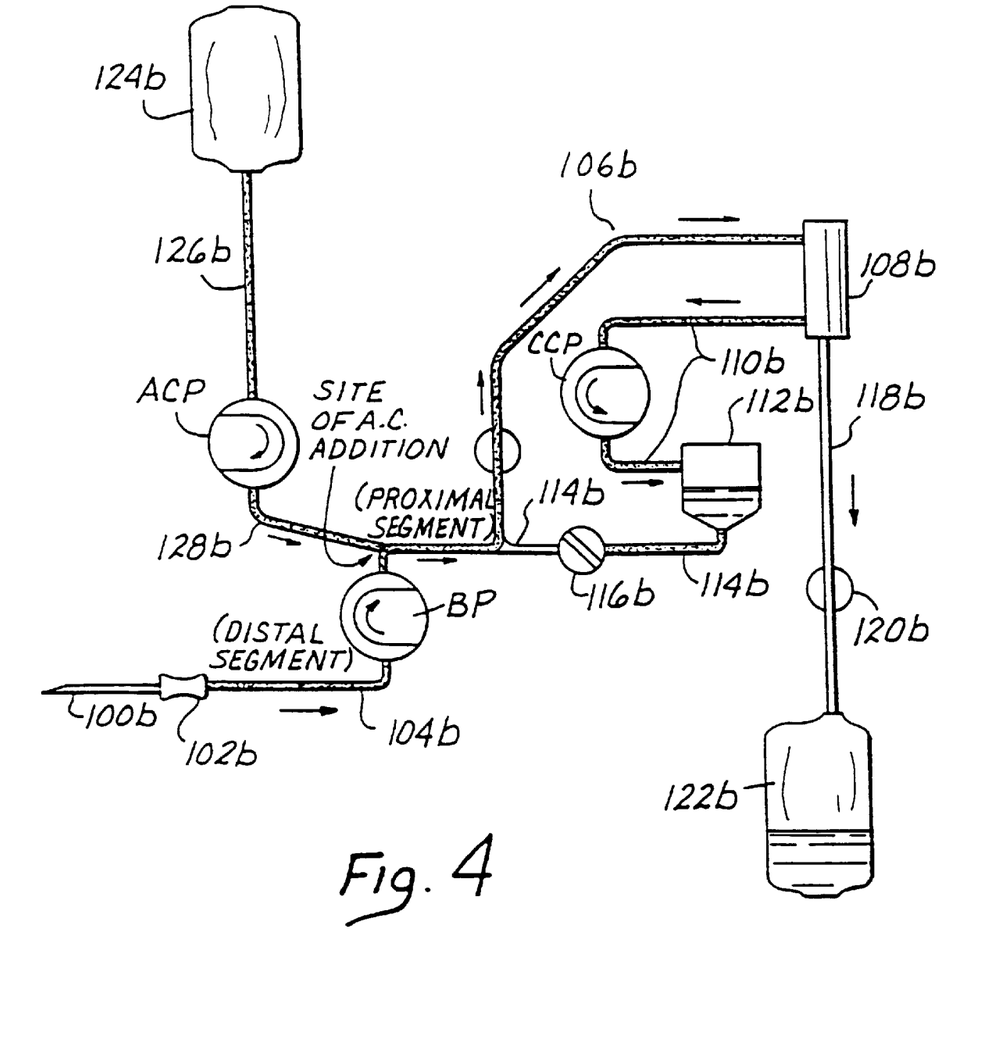
FIG. 4 is a component diagram of an automated, single-needle apheresis instrument of the present invention being operated in a blood withdrawal mode.

FIGS. 3 and 4 provide a side-by-side comparison of the typical operative components of a) an apheresis instrument of the prior art (FIG. 3) and b) an apheresis instrument of the present invention (FIG. 4). A blood withdrawal passageway or tube 104a, 106 connects the venipuncture needle 100a to an extracorporeal blood separator 108a. A blood pump BP, such as a peristaltic pump, is positioned on the blood withdrawal tubing to pump blood from the venipuncture needle 100a to the blood separator apparatus 108. The segment of blood withdrawal tubing connecting the hub 102a of the venipuncture needle 100a to the inlet of the blood pump BP is identified as the "distal segment" 104a. The segment of blood withdrawal tubing connecting the outlet of the blood pump to the inlet of the blood separation apparatus 108 is identified as the "proximal segment" 106. Negative pressure created on the inlet side of the blood pump bp serves to draw or pull blood from the venipuncture needle 100a through the distal segment 104a of the blood withdrawal tubing and into the blood pump BP. Thereafter, blood is expelled under positive pressure from the outlet side of the blood pump bp and is essentially "pushed" through the proximal segment 106 of the blood withdrawal tubing to the blood separation apparatus 108.

In the prior art system shown in FIG. 3, an anticoagulant bag or container 124a contains an anticoagulant solution such as a solution of heparin in 0.9% saline. An upper anticoagulant feed tube 126a connects the anticoagulant container 124a to the inlet side of anticoagulant pump ACP. A lower anticoagulant feed tube 128a connects the outlet side of anticoagulant pump ACP to the distal segment 104a of the blood withdrawal tube. Anticoagulant pump ACP is operated to pump a metered flow of anticoagulant from anticoagulant container 124a, through anticoagulant feed tubes 126a and 128a and into the distal segment 104a of the blood withdrawal tube wherein such anticoagulant solution becomes mixed with the blood being withdrawn through the distal segment 104a of the blood withdrawal tubing by blood pump BP. The anticoagulant pump ACP is typically operated in conjunction with the blood pump BP such that, whenever the blood pump BP is withdrawing blood from the patient, the anticoagulant pump ACP is simultaneously providing a metered flow of anticoagulant into such withdrawn blood.

In both the prior art system (FIG. 3) and the system of the present invention (FIG. 4), the blood/anticoagulant mixture passes through the proximal segment 106 of the blood withdrawal tube into the blood separator apparatus 108 wherein the blood is separated into a first component (e.g., cell concentrate) and a second component (e.g., plasma). The first component, such as cell concentrate, passes out of first component tube 110 and is pumped by a (shown on FIGS. 3 and 4 as the CCP) cell concentrate pump CCP to a reservoir 112. A reservoir outlet tube 114 connects the outlet port of reservoir 112 to the proximal 114 segment 106 of the blood withdrawal tube thereby providing a return loop for reinfusion of the cell concentrate, when desired. During withdrawal of blood, however, a clamp or valve 116 serves to close the reservoir outlet tube 114 thereby causing the cell concentrate or other blood component to pool within reservoir 112.

A second component, such as liquid plasma, exits the blood separation apparatus 108 through a second component outlet tube 118 and is collected in a bag or container 122. A second component line clamp 120 is positioned on the second component outlet tube 118 to permit stoppage of flow therethrough when desired.

One problem associated with the prior art apheresis system shown in FIG. 3 is the potential for inadvertent aspiration of air into the withdrawn blood through anticoagulant feed tubes 126a and/or 128a. This may occur when the anticoagulant container 124a is inadvertently allowed to become empty, or if the anticoagulant tube(s) 126a, 128a become broken or disconnected. Such may allow a quantity of air to pass downwardly through anticoagulant feed tube(s) 126a and/or 128a, into the distal segment 104a of the blood withdrawal tubing. Such inadvertently entrained air may then be pulled into the inlet side of blood pump BP and subsequently expelled or "pushed" by the blood pump BP through the proximal segment 106 of the blood withdrawal tubing. If undetected, such inadvertently entrained air may pass into the blood separator apparatus 108 and cause resultant interference with the blood separation process.

As shown in FIG. 4, the apheresis system of the present invention avoids the potential for inadvertently entrainment of air into the blood withdrawal tubing 104b, 106 through the anticoagulant feed tubes 126b, 128b by adding the anticoagulant solution from the lower anticoagulant feed tube 128b into the proximal segment 106 of the blood withdrawal tube rather than the distal segment 104b thereof. Because the proximal segment 106 of the blood withdrawal tube is on the outlet side of the blood pump BP, the blood passing through proximal segment 106 is under positive pressure. Accordingly, any inadvertently entrained air which passes through lower anticoagulant feed tube 128b to the site of its interconnection with proximal segment 106 of the blood withdrawal tube will not enter the proximal segment 106 of the blood withdrawal tube. Instead, under typical operating conditions, air within the lower anticoagulant feed tube 128b will become compressed by the positive pressure blood and blood will back up into the lower anticoagulant feed tube 128b from the proximal segment 106 of the blood withdrawal tube. Thus, the potential for inadvertent entrainment of air into the extracorporeal blood processing system is minimized.

ii. Incorporation of this Invention in Systems Having Automatic Air Detection Capability Many automated apheresis instruments are provided with air detectors mounted on the blood withdrawal tubing, or elsewhere, to detect any inadvertent aspiration of air into the extracorporeal blood processing system. Such air detectors are typically located some distance from the venipuncture needle through which the blood is withdrawn. Thus, even in systems which incorporate such air detectors, the inadvertent aspiration of air into the blood withdrawal line may result in an undetected void or air space within the blood withdrawal tubing, distal to the location of the air detector. Such inadvertently aspirated air may be subsequently reinfused into the patient on the following reinfusion cycle if it is not visually observed by the attendant technician or operator.

Figure 5:
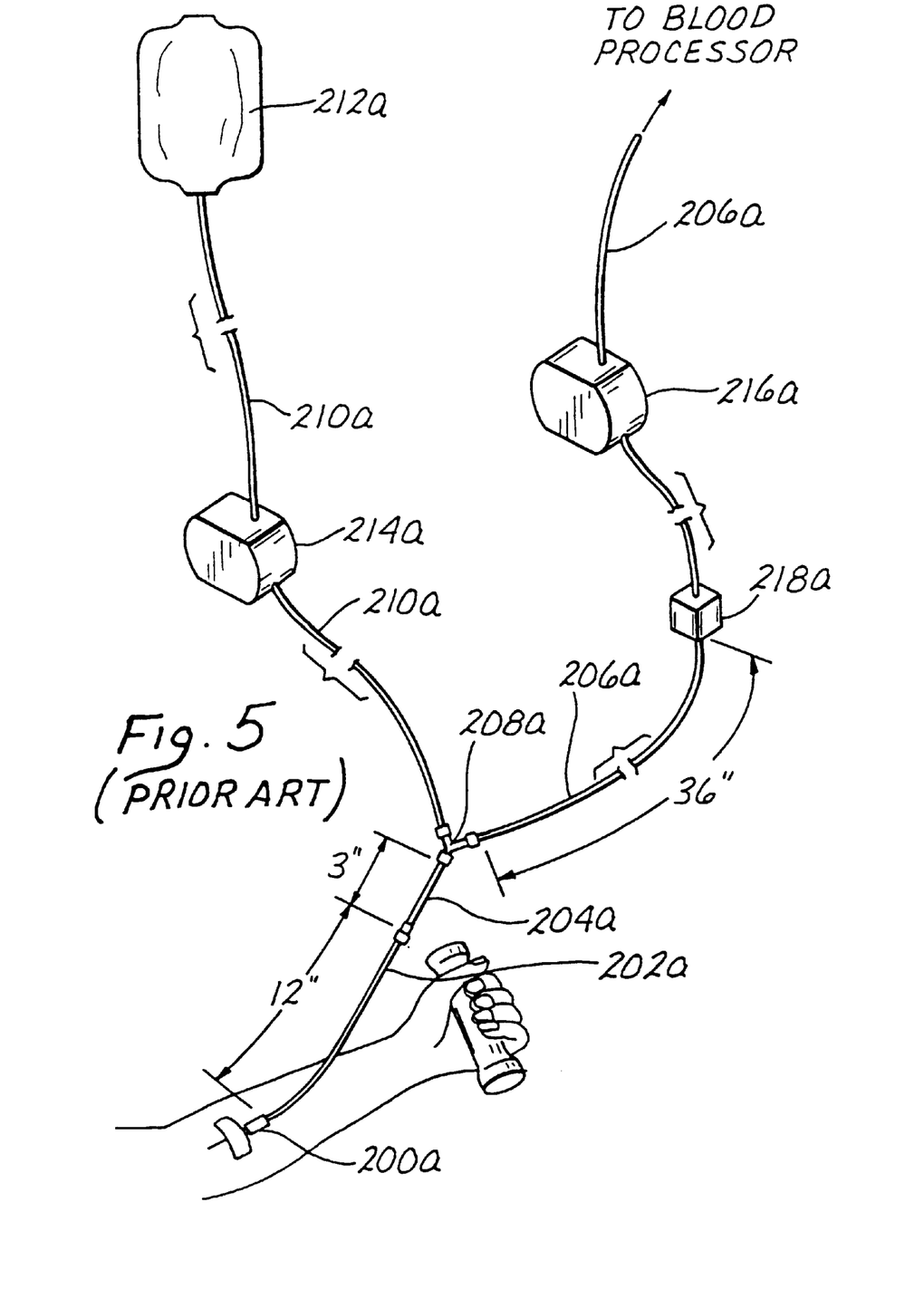
FIG. 5 is a perspective view of a partial tubing harness and related component portions of an apheresis instrument of the prior art.
Figure 6:
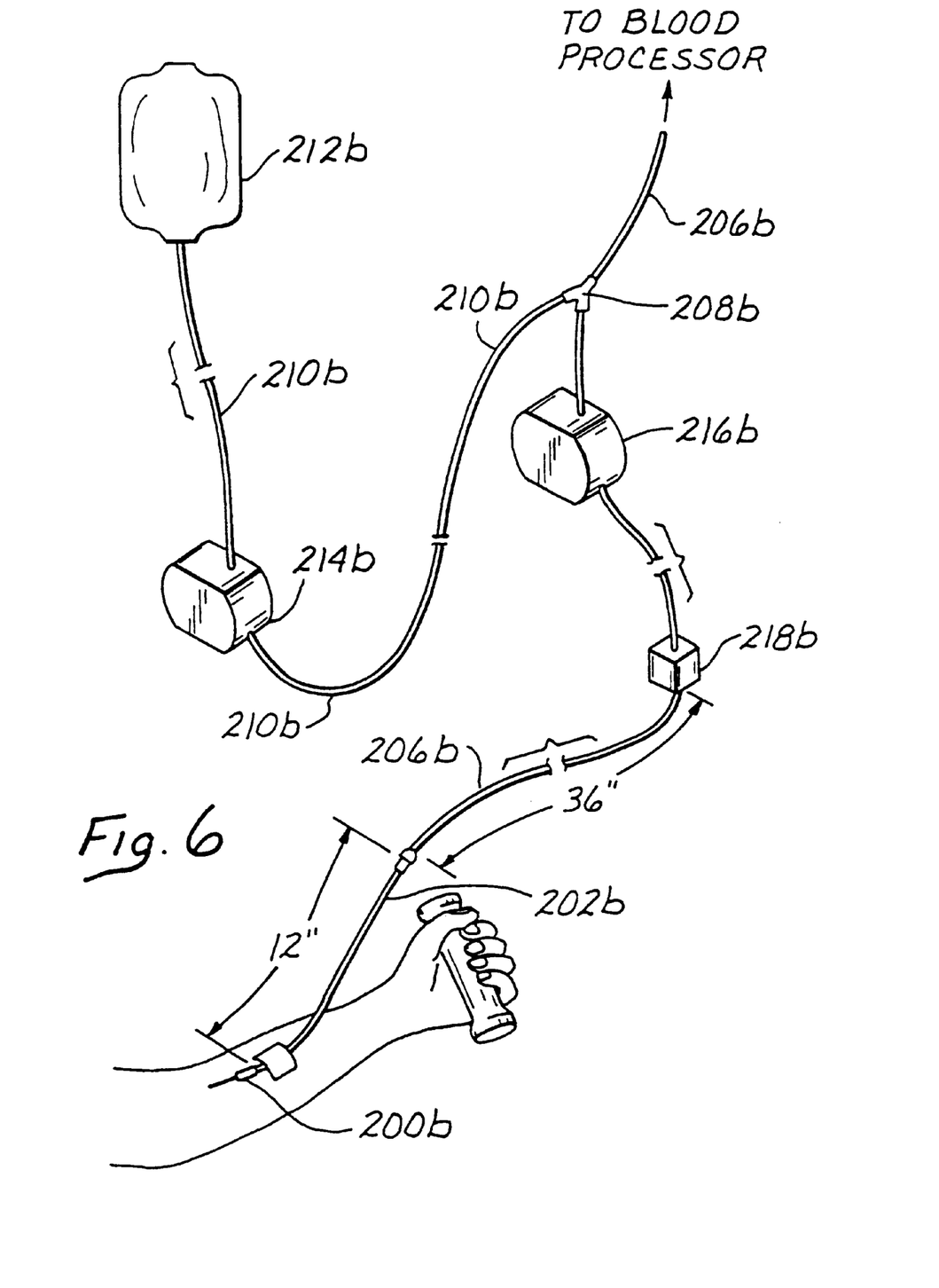
FIG. 6 is a perspective view of a partial tubing harness and related component portions of an apheresis instrument of the present invention.

FIGS. 5 and 6 show a comparison of a prior art apheresis instrument (FIG. 5) having an air detector operatively positioned on its blood withdraw line, and an apheresis instrument of the present invention (FIG. 6) having an air detector operatively positioned on its blood withdrawal line.

As shown in FIG. 5, the typical apheresis instrument of the prior art utilizes a venipuncture needle 200A as a means for intermittently withdrawing and infusing fluids out of/into the patient's blood vessel. An elongate tube or fistula 202A is connected at its distal end to the proximal hub of the venipuncture needle 202A, and at its proximal end to the distal connector of an extension tube 204A. The extension tube 204A is fluidly connected to the first arm of a tubular Y-connector 208A. The second arm of tubular Y-connector 208A is fluidly connected to anticoagulant feed tube 210A such that anticoagulant solution may be pumped from anticoagulant reservoir 212A, by anticoagulant pump 214A, through anticoagulant feed tube 210A and into the stream of blood being withdrawn through the fistula 202A and tubular extension 204A. The third arm of Y-connector 208A is fluidly connected to elongate blood withdrawal tube 206A. Elongate blood withdrawal tube 206A passes through blood pump 216A and subsequently carries the withdrawn blood to the extracorporeal blood processor. Thus, the "distal segment" of the blood withdrawal tube 206A extends from the third arm of the Y-connector 208A to the inlet side of blood pump 206A, while the "proximal segment" of the blood withdrawal tube 206A extends from the outlet side of blood pump 216A to the inlet of the extracorporeal blood processor (not shown). In the embodiment shown, the air detector 218A is positioned on the blood withdrawal tube 206A a distance of approximately 36 inches from the point at which the blood withdrawal tube 206A is connected to the third arm of the Y-connector 208A. Thus, if air is inadvertently drawn through anticoagulant feed line 210A into Y-connector 208A, such air must travel at least 36 inches up the blood withdrawal tube 206A to be detected by air detector 218A. Given this distance, it is clearly possible for inadvertently entrained air bubbles to be drawn into the segment of blood tubing 206A distal to the air detector 218A without triggering an alarm or being otherwise detected by air detector 218A. In the event of such inadvertent entrainment of air distal to the air detector, subsequent reversal of the blood pump 216A to reinfuse blood into the patient may result in infusion of such entrained air bubbles through the fistula 202A and into the patient's vasculature.

In an apheresis system of the present invention shown in FIG. 6, the proximal end of the fistula 202B is connected directly to the distal end of the blood withdrawal line 206B. As in the prior art system shown in FIG. 5, the air detector 218B is positioned approximately 36 inches from the distal end of the blood withdrawal tube 206B. In contrast, the device of the present invention shown in FIG. 6, incorporates an anticoagulant feed tube 210B which is connected to the "proximal segment" of the blood withdrawal tube 206B (i.e., on the outlet side of the blood pump) by way of tubular Y-connector 208B. As such, the anticoagulant feed tube 210B provides a flow of anticoagulant solution directly into the proximal segment of the blood withdrawal tube 206B wherein substantially continual positive pressure is maintained by the action of the blood pump 216B. As such, the anticoagulant pump 214B may be operated to pump a metered flow of anticoagulant solution from anticoagulant reservoir 212B, through anticoagulant feed tube 210B and into combination with the flow of blood being withdrawn through the proximal segment of the blood withdrawal tube 206B. In the event of inadvertent entrainment of air into the anticoagulant feed tube 210B, the positive pressure within the proximal segment of the blood withdrawal tube 206B will deter or prevent entry of such air from anticoagulant feed tube 210B into blood withdrawal tube 206B. Furthermore, there exists no possibility that air can be inadvertently drawn through anticoagulant feed tube 210B into that portion of blood withdrawal tube 206B lying distal to the air detector 218B, as is possible in the prior art system shown in FIG. 5. Thus, the potential for undetected reinfusion of air bubbles into the patient's vasculature is substantially minimized or eliminated by the system of the present invention.

The foregoing detailed description and the accompanying drawings are intended to describe certain specific embodiments of the present invention and do not purport to show or describe every possible embodiment in which the present invention may exist. Those skilled in the art will recognize that various modifications may be made to the herein described embodiments without departing from the spirit and scope of the present invention. Thus, it is intended that all such modifications and potential embodiments of the present invention be encompassed within the scope of the following claims and the equivalents thereof:

What is claimed is:

1. An apheresis system comprising:
    a venipuncture needle;
    a blood separator apparatus for separating whole blood into at least first and second blood fractions, said blood separator apparatus having an inlet through which whole blood may flow thereinto, a first outlet through which a first blood fraction may flow therefrom, and a second outlet through which a second blood fraction may flow therefrom;
    a blood tube which extends from said venipuncture needle to the blood separator apparatus;
    a reversible blood withdrawal/infusion pump mounted on said blood tube at a location between said venipuncture needle and said blood separator apparatus such that a distal segment of the blood tube extends from the venipuncture needle to the reversible blood withdrawal/infusion pump, and a proximal segment of the blood tube extends from the reversible blood withdrawal/infusion pump to the blood separator apparatus;
    said reversible blood withdrawal/infusion pump being alternately operable in a first direction to withdraw blood through the venipuncture needle and into the the inlet of the blood separator apparatus, and a second direction to infuse a blood fraction from one of the outlets of the blood separator apparatus through the venipuncture needle;
    an air detector positioned on the distal segment of the blood tube between the venipuncture needle and the reversible blood withdrawal/infusion pump; and,
    an anticoagulant feed tube connected to the proximal segment of the blood tube between the reversible blood withdrawal/infusion pump and the blood separator apparatus.

2. The system of claim 1 wherein the distal segment of the blood tube is treated with an anticoagulant substance, and the remainder of the blood tube is devoid of such anticoagulant substance.

3. The system of claim 2 wherein said anticoagulant substance is heparin.

4. The system of claim 1 wherein the distal segment of the blood tube as well as that portion of the proximal segment of the blood tube which extends from the reversible blood withdrawal/infusion pump to the location at which the anticoagulant feed tube is connected to the blood tube, are treated with an anticoagulant substance, and the remainder of the blood tube is devoid of such anticoagulant substance.

5. The system of claim 4 wherein said anticoagulant substance is heparin.

6. The system of claim 1 wherein an anticoagulant pump is mounted on the anticoagulant feed tube to pump anticoagulant into the proximal segment of the blood tube.

* * * * *